(12) United States Patent
Harada et al.

(10) Patent No.: US 8,675,187 B2
(45) Date of Patent: Mar. 18, 2014

(54) PHOTOMETER AND ANALYZING SYSTEM PROVIDED WITH PHOTOMETER

(75) Inventors: Kunio Harada, Hachioji (JP); Sakuichiro Adachi, Kawasaki (JP); Isao Yamazaki, Ryugasaki (JP)

(73) Assignee: Hitachi High-Technologies Corporation, Tokyo (JP)

( * ) Notice: Subject to any disclaimer, the term of this patent is extended or adjusted under 35 U.S.C. 154(b) by 56 days.

(21) Appl. No.: 13/141,378

(22) PCT Filed: Dec. 22, 2009

(86) PCT No.: PCT/JP2009/007096
§ 371 (c)(1),
(2), (4) Date: Jun. 22, 2011

(87) PCT Pub. No.: WO2010/073604
PCT Pub. Date: Jul. 1, 2010

(65) Prior Publication Data
US 2011/0255090 A1 Oct. 20, 2011

(30) Foreign Application Priority Data

Dec. 24, 2008 (JP) ................................. 2008-326796

(51) Int. Cl.
*G01J 1/00* (2006.01)
(52) U.S. Cl.
USPC ........................................................... 356/213
(58) Field of Classification Search
USPC ...................... 356/36–42, 213–236, 244–246, 356/436–442
See application file for complete search history.

(56) References Cited

U.S. PATENT DOCUMENTS

| | | | | |
|---|---|---|---|---|
| 4,935,875 A | * | 6/1990 | Shah et al. ...................... | 702/22 |
| 2004/0207841 A1 | | 10/2004 | Yoshida | |

FOREIGN PATENT DOCUMENTS

| | | |
|---|---|---|
| JP | 60-114743 | 6/1985 |
| JP | 08-075648 | 3/1996 |
| JP | 3749321 | 12/2005 |
| JP | 2007-155477 | 6/2007 |
| JP | 3964291 | 6/2007 |
| JP | 2007-198935 | 8/2007 |
| JP | 2007-218633 | 8/2007 |
| JP | 2007-218883 | 8/2007 |
| JP | 2007-225339 | 9/2007 |
| JP | 2007-304103 | 11/2007 |
| JP | 2008-134128 | 6/2008 |
| WO | WO 96/17243 | 6/1996 |

OTHER PUBLICATIONS

Japanese Office Action dated Aug. 27, 2013 for Application No. 2010-543846.

\* cited by examiner

*Primary Examiner* — Tara S Pajoohi Gomez
(74) *Attorney, Agent, or Firm* — Antonelli, Terry, Stout & Kraus, LLP.

(57) ABSTRACT

In an analysis system for detecting amounts of components contained in samples, many samples can be measured simultaneously in the whole of the system by use of compact inexpensive photometers. An LED with low heat generation and a long life span is used as a light source. Compactness is achieved by bended optical axis instead of a straight one. Components for bending an optical axis and components for condensing light to ensure an amount of light are in common use to reduce the number of components. Compactness, reduction of the number of components, and integration achieve easy optical axis alignment and precise measurement.

21 Claims, 22 Drawing Sheets

(a)

PARABOLIC
MIRROR (b)

ELLIPTIC
MIRROR

| MODEL NAME | THE NUMBER OF LIGHTS | OUTPUT | FIGURE | LIGHT AMOUNT RATIO |
|---|---|---|---|---|
| PARABOLIC MIRROR | 100,000 | 2.29E-03 | (a) | 1 |
| ELLIPTIC MIRROR | 100,000 | 2.91E-03 | (b) | 1.27 |

PHOTOMETER AND ANALYZING SYSTEM PROVIDED WITH PHOTOMETER

TECHNICAL FIELD

The present invention relates to a liquid analysis system for detecting amounts of components contained in a sample and to a technology for making a photometer, which is a main of the system, compact and inexpensive and for making the entirety of the liquid analysis system inexpensive.

BACKGROUND ART

As an analysis device for detecting amounts of components contained in a sample, a spectrometer is widely used in which a sample solution in a reaction vessel is illuminated with white light from, e.g., a halogen lamp, the light passing through the sample solution is dispersed by a diffraction grating to obtain a required wavelength component, and its optical absorbance is determined to measure an amount of a target component. Alternatively, white light may be dispersed by a diffraction grating and then a sample solution may be illuminated with the light. As one example, Patent Literature 1 discloses an automatic analysis device.

Patent Literature 1 and Patent Literature 2 disclose analysis devices as examples in which a lens and a mirror are used to condense light from a light source of, e.g., a halogen lamp and to illuminate a sample precisely with the light.

As an analysis device using an LED as a light source instead of the halogen lamp, Patent Literature 4 discloses an analysis instrument and Patent Literature 5 discloses an analysis device.

Patent Literature 6 discloses an analysis device as an example using an LED as a light source and using a lens to condense light of the LED and to illuminate a sample with large amounts of light.

CITATION LIST

Patent Literature

Patent Literature 1: U.S. Pat. No. 3,749,321
Patent Literature 2: Japanese Patent Application Laid-Open Publication (JP-A) No. 2007-225339
Patent Literature 3: Japanese Patent Application Laid-Open Publication (JP-A) No. 2007-218883
Patent Literature 4: U.S. Pat. No. 3,964,291
Patent Literature 5: Japanese Patent Application Laid-Open Publication (JP-A) No. 2007-198935
Patent Literature 6: Japanese Patent Application Laid-Open Publication (JP-A) No. 2007-225339

SUMMARY OF INVENTION

Technical Problem

In the example using a halogen lamp in the above-mentioned related arts, there is a problem that cooling is required because of heat generation of the halogen lamp and precise temperature control using, e.g., cooling water is required to obtain a stable amount of light. There is also a problem that replacement of a halogen lamp is required because the lamp has a short life span and then the replacement is a burden to a user of the device and thus that the layout needs to be considered on the assumption of the lamp replacement in device design to decrease the flexibility of device design.

In an optical system using a halogen lamp, there is also a problem that it is difficult to align an optical axis because many components such as a diffraction grating used to disperse white light from a halogen lamp and a lens and mirror used to condense light from a light source and to illuminate a sample precisely with the light are used.

The analysis instrument of Patent Literature 4 and analysis device of Patent Literature 5 each use an LED as a light source and have a simple structure using only an LED and a detector, but there is a problem that an amount of light for illuminating a sample is small because a lens, a mirror, etc. for condensing light are not used actively and precise analysis is difficult depending on a purpose of analysis.

In the analysis device of Patent Literature 6, which is the above related example using an LED as a light source and a lens to ensure an amount of light by light condensation, multiple photometer units are provided on one stage densely. Therefore, there is a problem that assembly alignment is difficult and there is a problem that it is difficult to respond to the case in which one or some of the multiple photometry units need to be replaced for a change of a wavelength and for maintenance. Additionally, since an optical axis is on one straight line, the occupied area of the reaction table in the radial direction is large.

To build an LED photometer, at least a light source, a condensing lens, a slit, and a photo detector shown in FIG. 1 are required. (A reaction vessel and a sample are not included in the photometer.) The structure using only a light source and photo detector is possible. For precise analysis, condensing components (a lens and a mirror) for ensuring an amount of light are indispensable. To define a cross sectional shape of a light beam and make the amount of light passing through a sample constant or to restrict stray light from entering a detector, a slit is also indispensable. In an automatic biochemistry analyzer for precise analysis using a photometer, to keep a sample temperature in a reaction vessel constant, the reaction vessel is immersed in constant temperature water circulating in a thermostatic bath. To test many samples in short time, multiple reaction vessels are arranged circumferentially to form an integrated reaction vessel disk. The test by a photometer section is conducted while the reaction vessel disk circulates in a ring shaped thermostatic bath concentric with the reaction vessel disk. FIG. 2 shows only one side of vertical cross sections of a ring-shaped thermostatic bath in an example in which the LED photometer of the above minimum structure is disposed on the thermostatic bath. The thermostatic bath needs a window formed of a transparent member for passing-through the measurement light without leaking constant temperature water.

When the LED photometer of the minimum structure is disposed on the thermostatic bath, the light source and condensing lens are disposed outside the ring-shaped thermostatic bath and the photo detector is disposed inside the thermostatic bath as shown in FIG. 2. The positional relationship of the light source and photo detector relative to the thermostatic bath may be reverse. Since it is desirable that the slit is as close to the reaction vessel as possible, the slit is disposed inside the thermostatic bath.

To maintain the components in their set positions and to make easy the alignment of the optical axis and the assembling, it is desirable that the components of the photometer are assembled integrally to a support/holder, which is attached to the thermostatic bath, as shown in FIG. 3.

However, to attach the support/holder to the thermostatic bath, there is a problem that it is necessary to gouge the thermostatic bath greatly and sealing for preventing leakage of the constant temperature water etc. thus becomes complicated.

FIG. 4 shows a state in which the components except the slit are integrated and attached to the thermostatic bath. In such a state, it is not necessary to gouge the thermostatic bath.

A window formed of a transparent member to pass measurement light through without leaking constant temperature water may be provided. However, since the optical axis alignment needs to be conducted in combination with the slit, the optical axis alignment is needed after attaching the integrated components to the thermostatic bath. It is possible to align an optical axis by mechanical precision of the components. As compared to when only the retaining member of FIG. 3 and the components attached thereto are adjusted by mechanical precision, the slit and the integrated components except the slit need to be precisely attached to the thermostatic bath respectively in the example of FIG. 4. Therefore, there is a problem that the thermostatic bath usually having a diameter of 300 mm or over needs high precision.

One of objects of the present invention is to contribute to downsizing of the device and to improvement of flexibility of device design. When using a semiconductor light source such as a light emitting diode and a semiconductor laser as a light source, a photometer structure suitable for a semiconductor light source is applied to an analysis device. Accordingly, downsizing of the device can be further facilitated and design flexibility of the device can be improved.

Solution to Problem

For addressing the problems, a photometer is characterized in including: a light source; a first support transmitting and passing through light emitted from the light source; a detector for detecting light passed through a reaction vessel containing a measurement sample; a second support provided with the detector, the first support and the second support being disposed such that the reaction vessel containing a measurement sample is inserted therebetween; a first reflection section provided to the first support, reflecting light emitted from the light source, and passing the light through the reaction vessel; and a condensing section for condensing light emitted from the light source and passing the light through the reaction vessel.

An analysis system is characterized that includes: a reaction vessel for containing a measurement sample; a thermostatic bath containing a constant temperature fluid that immerses therein and retains the reaction vessel; and a photometer on the bottom portion of the thermostatic bath to illuminate the reaction vessel with light. The photometer includes: a light source; a first support transmitting and passing light emitted from the light source therethrough; a detector for detecting light passed through a reaction vessel containing a measurement sample; a second support provided with the detector; and a reflection portion provided to the first support, reflecting light emitted from the light source, and passing the light through the reaction vessel, the first support and the second support being disposed such that the reaction vessel containing a measurement sample is inserted therebetween.

The reflection section can use a plane mirror, a parabolic mirror, an elliptic mirror, etc., which can be arranged depending on each feature.

A light emitting diode and semiconductor diode generating less heat and having a long life span are used as the light source. An optical axis is not on a straight line but is bent for downsizing. A component for bending the optical axis and a component for condensing light to ensure an amount of light are in common use to reduce the number of components. The downsizing, the reduction of the number of the components, and the integration make the alignment of the optical axis easy. Accordingly, a more precise photometer and analysis system is achieved.

Advantageous Effects of Invention

According to one embodiment the present invention, by bending an optical axis by use of a reflector, radial sizes of a thermostatic bath of a photometer and a reaction vessel disk can be reduced to contribute to downsizing of the device. Additionally, a condensing lens becomes unnecessary by bending an optical axis by use of a parabolic mirror and an elliptic mirror, the number of components can thus be reduced, and cost reduction becomes possible together with the ease of optical axis alignment. Further, by using a parabolic mirror and an elliptic mirror properly, it becomes possible to use properly a photometer oriented to an amount of light influencing detection sensitivity and a photometer oriented to a characteristic of measurement of a scattering item. The technology for improving a capability of the system can be provided.

DESCRIPTION OF EMBODIMENTS (Embodiment 1)

Figure 1:
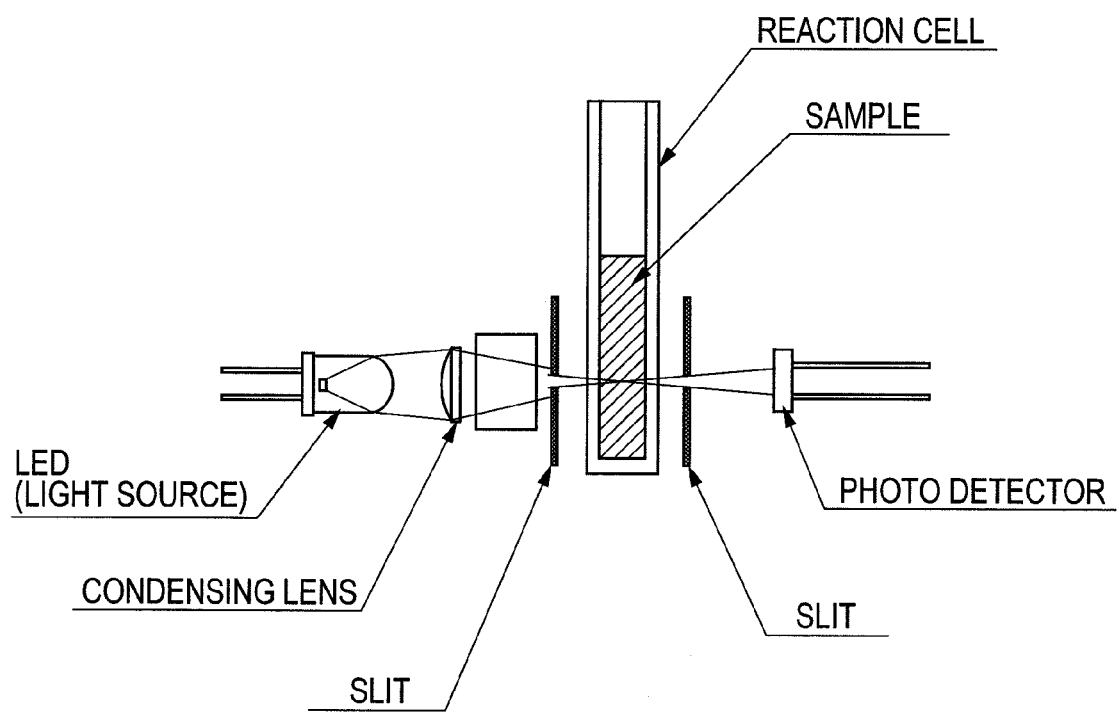
FIG. 1 is a diagram showing the minimum structure required for an LED photometer.
Figure 2:
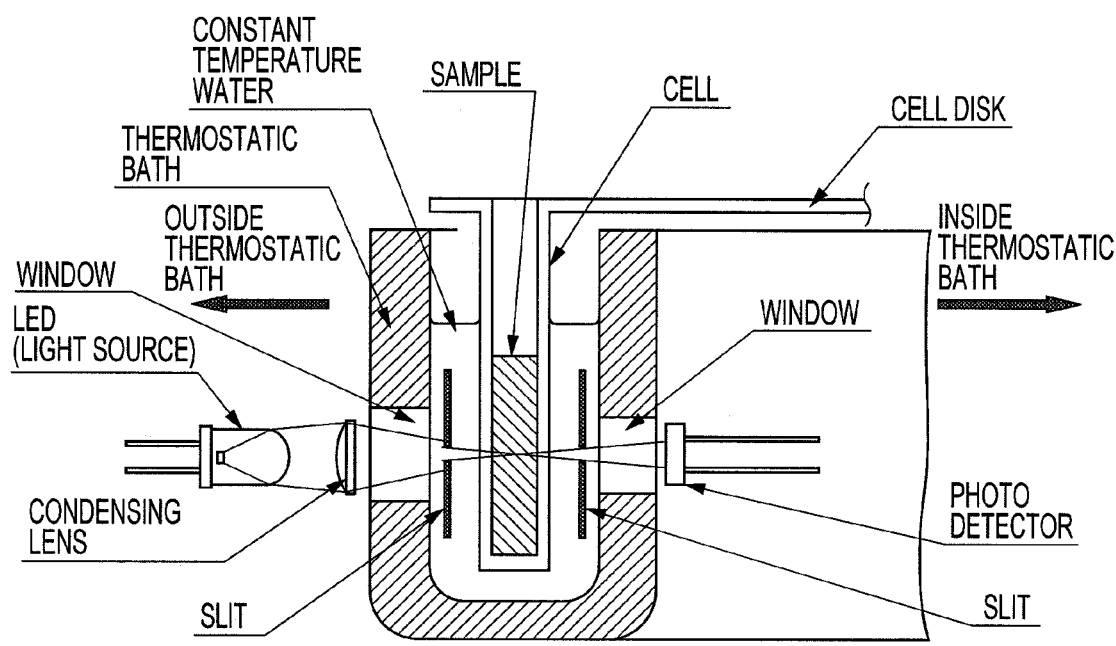
FIG. 2 is a diagram of an example in which the LED photometer of the minimum structure is disposed on a thermostatic bath.
Figure 3:
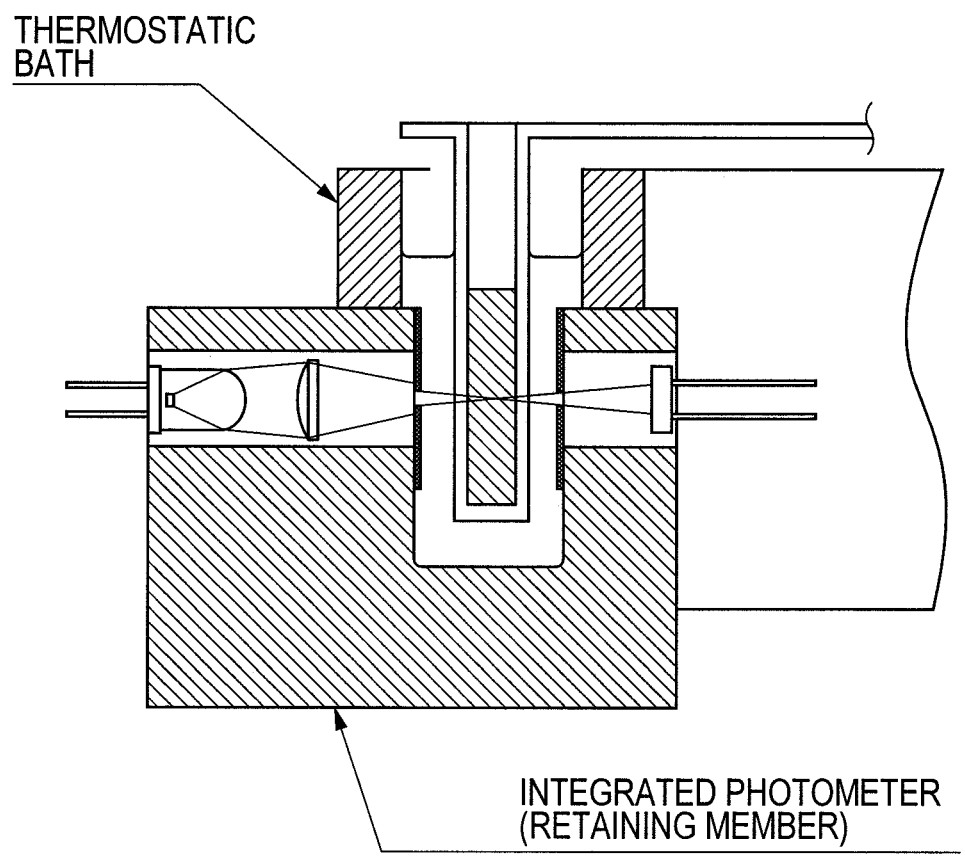
FIG. 3 is a diagram of an example in which the LED photometer of the minimum structure is integrated and disposed on the thermostatic bath.
Figure 4:
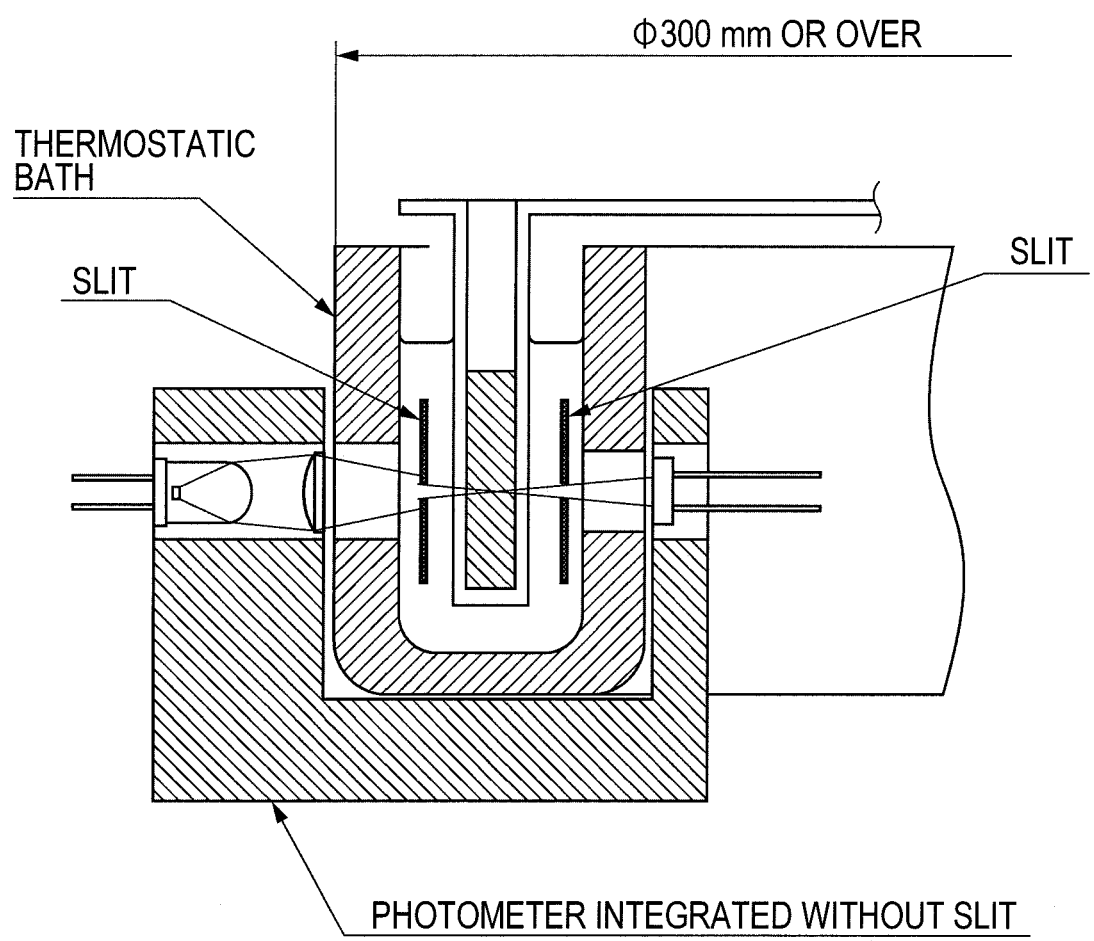
FIG. 4 is a diagram of the example in which the LED photometer of the minimum structure except a slit is integrated and disposed on the thermostatic bath.
Figure 5:
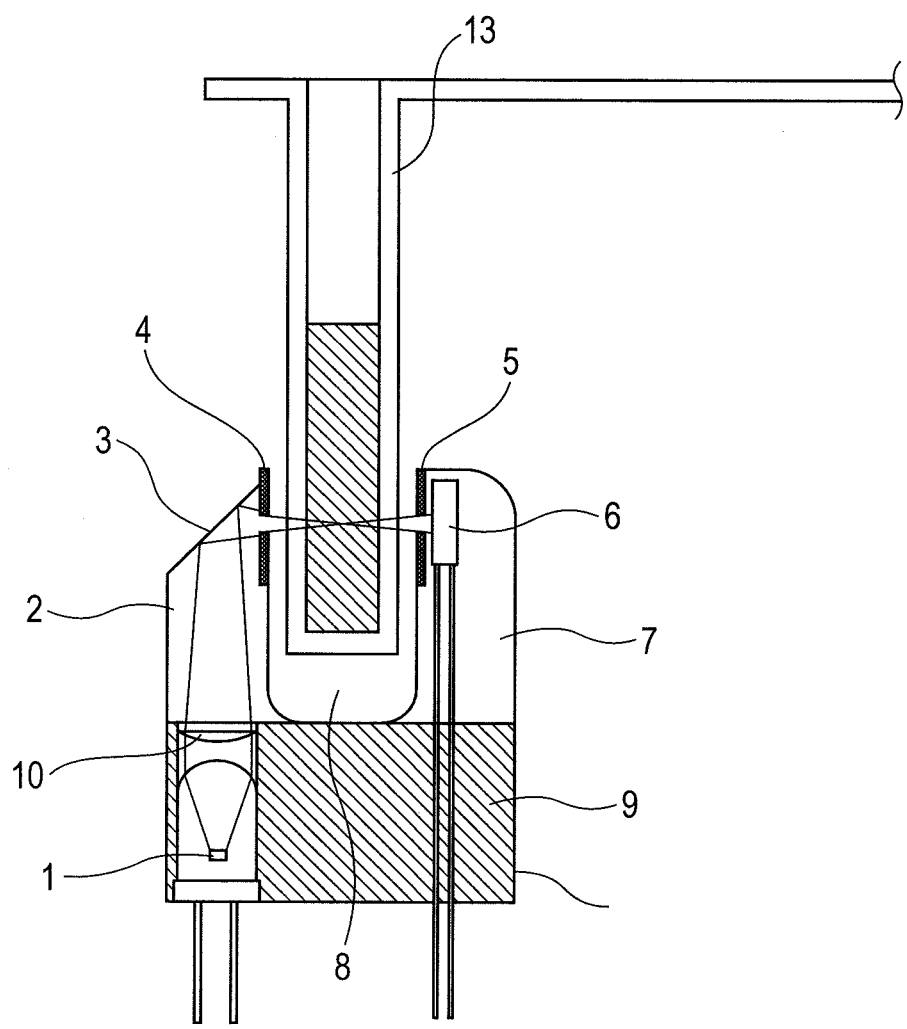
FIG. 5 is a diagram showing a structure of a photometer for a liquid analysis system according to the present invention.

FIG. 5 is a diagram showing a structure of a photometer for a liquid analysis system according to the present invention (hereinafter described as a photometer). The present photometer is a photometer 11 including: an LED source 1; a first support 2 for transmitting or passing light emitted from the LED source 1 therethrough; a first reflector 3 provided to the first support 2; a first slit 4 provided to the first support 2; a second support 7 provided with a second slit 5 and a photo detector 6; a third support 9 for connecting the first support 2 and the second support 7 between which a reaction vessel 13 is disposed a slot 8 is formed; and a condensing lens 10 held by the first support 2 or the third support 9. As a light source, a light emitting diode (LED) is used in this example, but a semiconductor laser etc. can be also used.

The analysis of a measurement sample is conducted by the present photometer 11 attached to a thermostatic bath of a liquid analysis system. Therefore, before explanation of an analysis method, the structure around near a portion where the present photometer of the liquid analysis system is attached and the positional relationship between the portion and the present photometer are explained.

Figure 6:
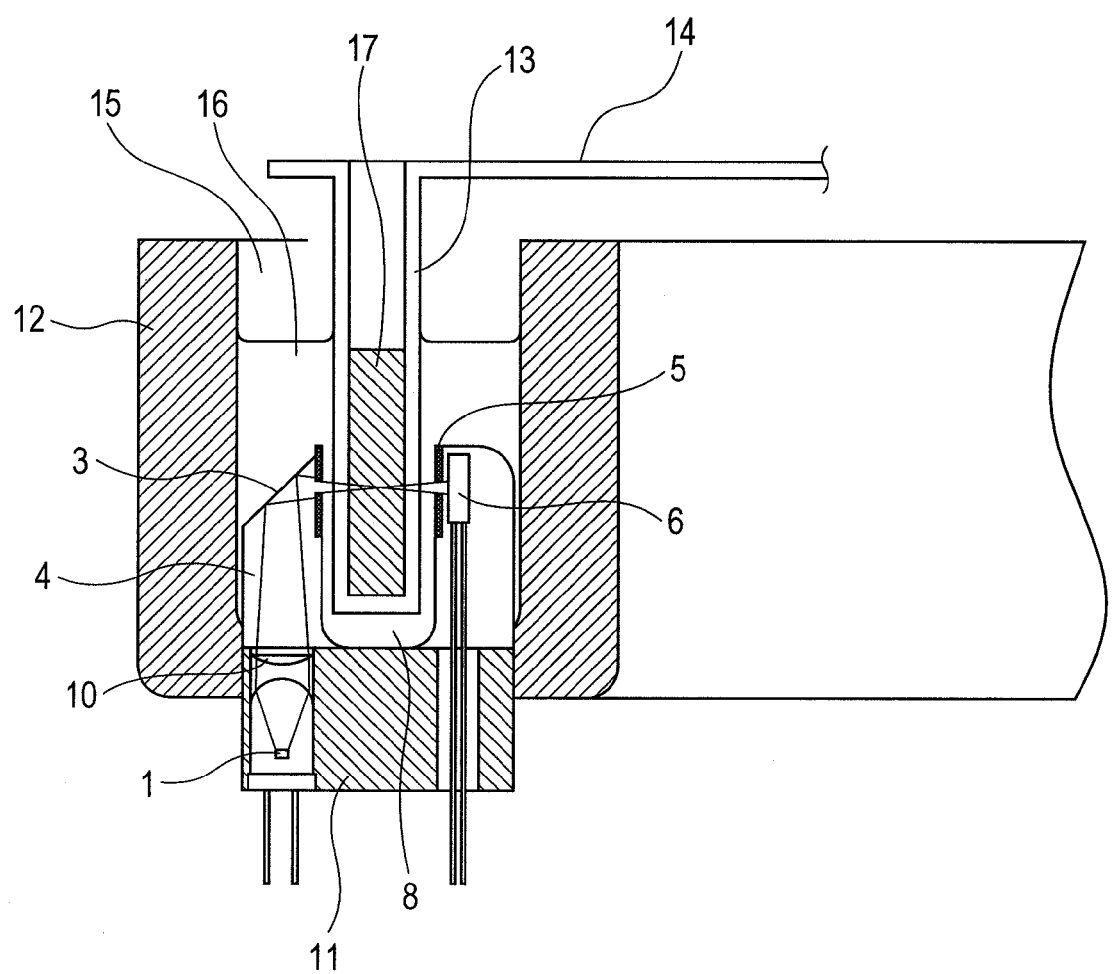
FIG. 6 is a diagram showing a structure in which the photometer for the liquid analysis systems according to the present invention is attached to the thermostatic bath.

FIG. 6 shows part of the liquid analysis system, and shows only one side of vertical sections of a ring shaped thermostatic bath 12 having a U shaped cross section and one side of vertical sections of a reaction vessel disk 14 having multiple reaction vessels 13 arranged on a circumference concentric with the thermostatic bath 12. The reaction vessel 13 has a light incident surface, a light transmission inner surface, and a light emitting surface, which are arranged parallel to each other and rectangular to an optical axis. The thermostatic bath 12 has a flow path 15 having a U shaped cross section. Constant temperature water 16 kept at a constant temperature circulates in the flow path 15 at a constant liquid level. The reaction vessel disk 14 rotates around a common central axis with the thermostatic bath 12 above the thermostatic bath 12. The reaction vessel 13 mounted to the reaction vessel disk 14 is submerged in the constant temperature water 16 in the thermostatic bath 12, and moves inside the flow path 15 of the thermostatic bath 12. A measurement sample 17 is placed in the reaction vessel 13 for measurement. The photometer 11 is attached to the thermostatic bath 12 from the lower side of the thermostatic bath 12 such that the reaction vessel 13 is movable inside the slot 8. One or multiple photometers 11 are disposed on a circumference concentric with the thermostatic bath 12.

Analysis of measurement samples by the photometer 11 is conducted when the photometer 11 is attached to the thermostatic bath 12 as mentioned above, the reaction disk 14 rotates, and the reaction vessel 13 containing the target measurement sample 17 moves to a position of the slot 8 of photometer 11.

In the analysis, light emitted from the LED source 1 is condensed to a position of the measurement sample 17 in the reaction vessel 13 by the condensing lens 10, and reflected by the first reflector 3 to bend the optical axis by substantially 90 degrees. Then, the light illuminates an illumination area controlled to be constant by the first slit 4.

To prevent, e.g., bacterial growth, alkali or acid liquid is usually used for the constant temperature water 16. Therefore, the first support 2, the first reflector 3, the first slit 4, the second slit 5, and the third support 9 use glass, metal, and/or resin which are resistant to alkali liquid and acid liquid. The LED source 1, the photo detector 6, the condensing lens 10, etc. are sealed to prevent the intrusion of the constant temperature water 16.

The measurement principle of samples by the analysis system, which is the target of the present photometer, is as follows.

A reagent selected by an analysis item is mixed with the measurement sample 17, and reacts with an analyte component, and absorbs light of a predetermined wavelength in accordance with a ratio of a contained analyte component. Therefore, a wavelength of light emitted from the LED source 1 uses a wavelength selected from analysis items. The light illuminating the measurement sample 17 is absorbed by an amount of an analyte component as mentioned above, and illuminates the photo detector 6 after stray light is removed by the second slit 5. The light illuminating the photo detector 6 is changed into an electrical signal by the photo detector 6, and an amount of the analyte component contained in the measurement sample 17 can be obtained by analyzing an amount of the signal. Usually, such measurement is called an absorbance measurement.

Figure 7:
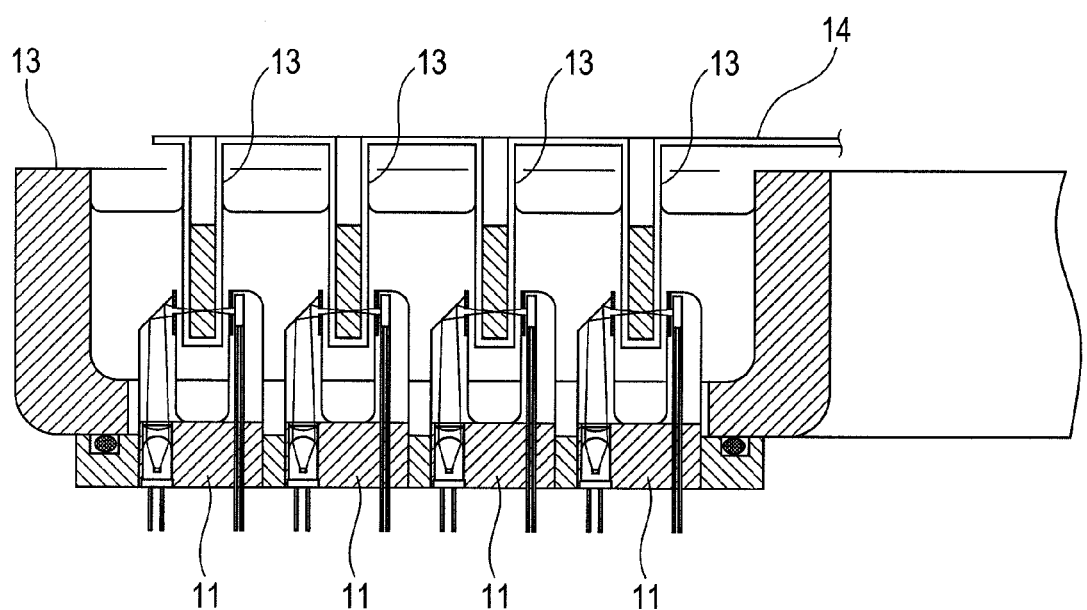
FIG. 7 is a diagram showing multiple photometers for the liquid analysis system according to the present invention are attached to the thermostatic bath.

According to the photometer 11, in the photometer as shown in FIGS. 1 to 4, by bending an optical axis by the first reflector 3 and disposing the photo detector 6 immediately after the second slit 5, it is possible to reduce radial sizes of the thermostatic bath 12 of the photometer and reaction vessel disk 14. Accordingly, it becomes possible to further arrange the multiple reaction vessels 13 located on the circumference of the reaction vessel disk 14 and the multiple photometers 11 in multiple rows concentrically as shown in FIG. 7. The processing capability can be improved without changing a size of the device or the device can be made compact without changing the processing capability. Analyses of multiple items can be simultaneously conducted by respectively changing wavelengths of the multiple photometers.

Figure 8:
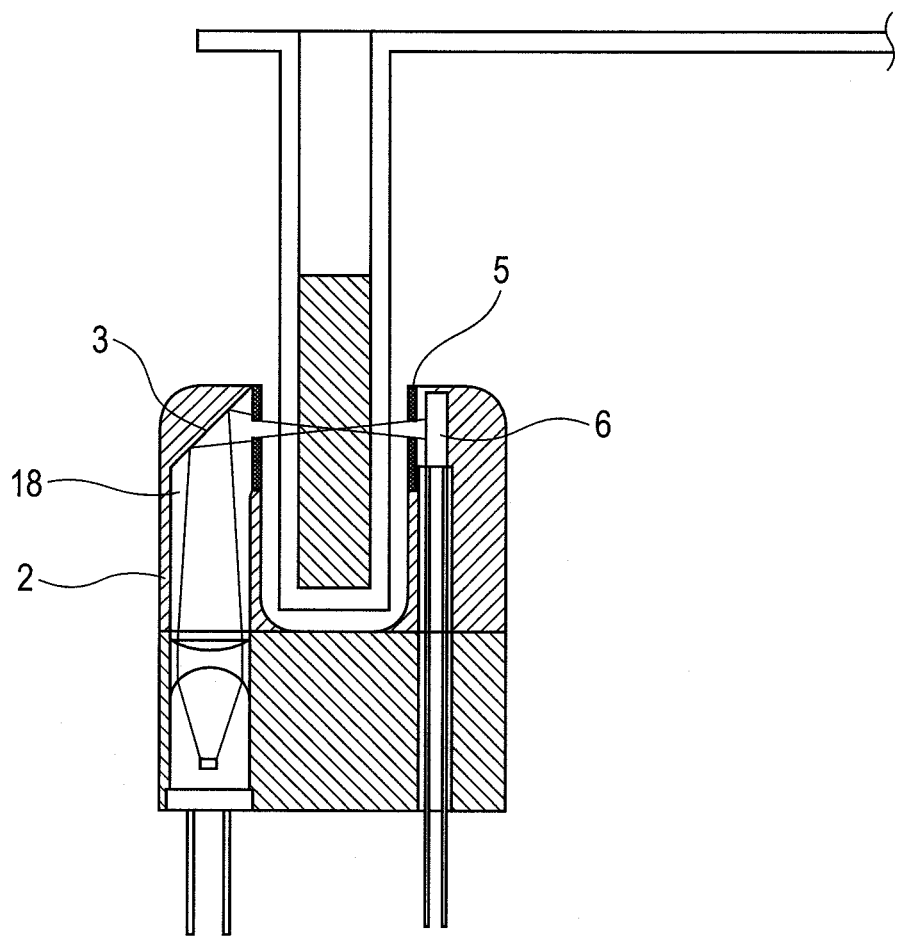
FIG. 8 is a diagram showing a structure of the photometer for the liquid analysis system according to the present invention.

The example of FIG. 5 explains the first support 2 using the optical transmission member. The first reflector 3 uses its external surface as a reflective surface. As shown in FIG. 8, the structure can be considered in which the first support 2 uses an opaque member, inside which a space 18 passing light therethrough is provided. This increases options of methods of manufacturing components, and cost reduction is expectable.

Figure 9:
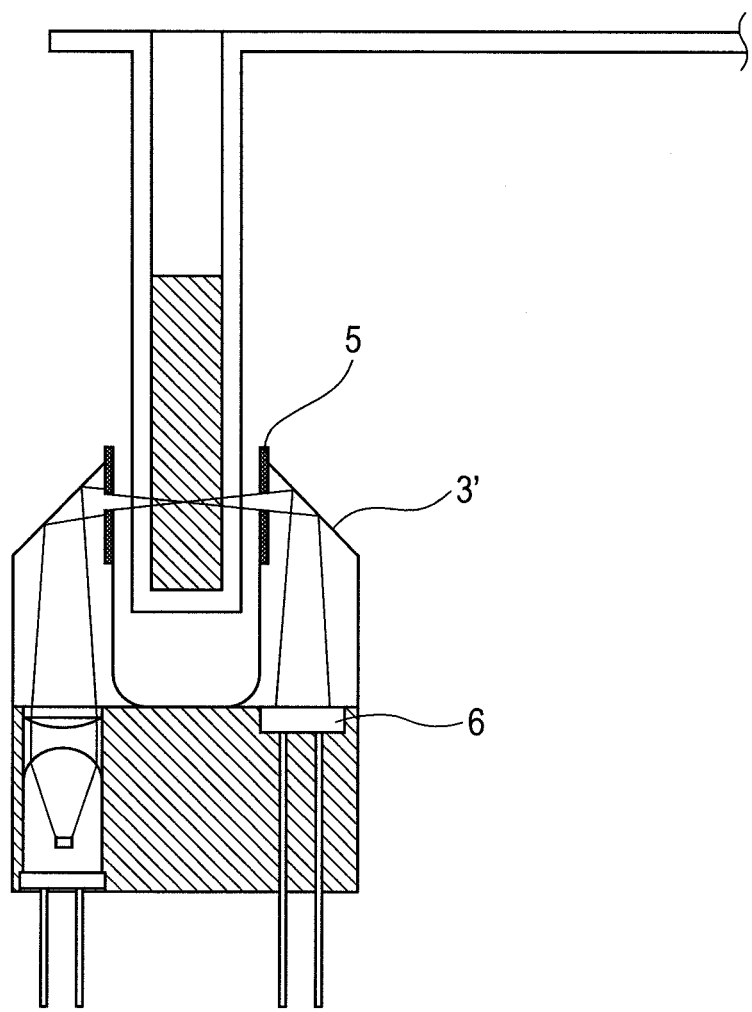
FIG. 9 is a diagram showing a structure of the photometer for the liquid analysis systems according to the present invention.

In FIG. 5, the photo detector 6 is disposed immediately after the second slit 5. Stray light is easily detected when the second slit 5 and photo detector 6 are too close to one another. As shown in FIG. 9, it is also possible for a second reflector 3' to bend an optical axis downward.

(Embodiment 2)

Figure 10:
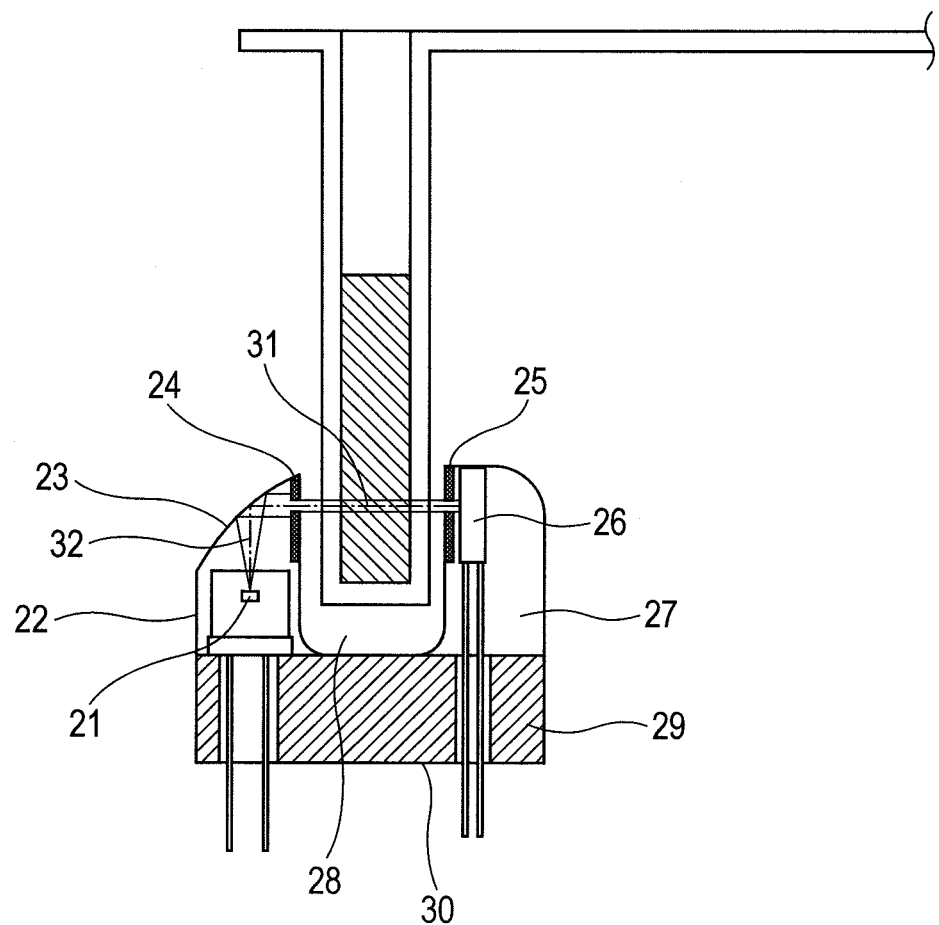
FIG. 10 is a diagram showing a structure of the photometer for the liquid analysis system according to the present invention.

FIG. 10 is a diagram showing a structure of the photometer according to the present invention. The present photometer is a photometer 30 including: an LED light source 21; a first support 22 for transmitting or passing light emitted from the LED light source 21 therethrough; a first reflector 23 provided to the first support 22; a first slit 24 also provided to the first support 22; a second support 27 provided with the second slit 25 and photo detector 26; and a third support 29 connecting the first support 22 and the second support 27 between which a slot 28 is formed. The light emitting diode (LED) is exampled as the light source, but a semiconductor laser etc. can be also used.

The first reflector 23 has a shape of a partially cutaway parabolic mirror. An axis of the parabolic mirror is set substantially horizontally, and in parallel with a straight line connecting the centers of the first slit 24 and the second slit 25, namely with a horizontal optical axis 31. The LED light source 21 is disposed in a focal point of the parabolic mirror.

An optical axis 32 of light emitted from the LED light source 21 is set generally vertically, and bent at a right angle by the first reflector 23 to be the horizontal optical axis 31.

Analysis of a test sample by the photometer 30 is conducted by attaching the photometer 30 to the thermostatic bath of the liquid analysis system. The positional relationship between the structure of the liquid analysis system near the portion to which the present photometer is attached and the present photometer is the same as that of Embodiment 1, and is thus not explained.

Similarly to Embodiment 1, analysis of a test sample by the photometer 30 is conducted when the photometer 30 is attached to the thermostatic bath 12, the reaction disk 14 rotates, and the reaction vessel 13 containing the target measurement sample 17 moves to the slot 28 of the photometer 30.

In the analysis, light emitted from the LED light source 21 is reflected by the first reflector 23, an illumination area is controlled to be constant by the first slit 24, and the light illuminates the measurement sample 17 in the reaction vessel 13. The first reflector 23 is a parabolic mirror. The light emitted from the LED light source 21 and disposed at its focal point is reflected and bent by the first reflector 23, and then shaped and condensed in parallel with the horizontal optical axis 31. Strictly, since the LED light source 21 is not a perfect point source, the light emitted from a position offset from the focal point of the parabolic mirror is not completely parallel to the horizontal optical axis 31. An amount of the light passing through both of the first slit 24 and the second slit 25 from the parabolic mirror may be condensed generally in parallel.

To prevent bacterial growth etc., alkali or acid liquid is usually used for the constant temperature water 16. Therefore, the first support 22, the first reflector 23, the first slit 24, the second slit 25, and the third support 29 use glass, metal, and/or resin which are resistant to alkali and acid fluids. The LED light source 21 and the photo detector 26 are sealed to prevent the intrusion of the constant temperature water 16.

The principle for measurements of samples by the liquid analysis system to which the present photometer is directed is the same as that of Embodiment 1, and thus not explained.

Also in the photometer 30, radial sizes of the thermostatic bath 12 of the photometer and the reaction vessel disk 14 can be reduced relative to the photometer shown in FIGS. 1 to 4. Similarly to FIG. 7, the multiple reaction vessels 13 arranged on the circumference of the reaction vessel disk 14 can be arranged in multiple rows concentrically. The processing capability can be improved without changing the size of the device or the device can be improved without changing the processing capability.

In Embodiment 1, the first reflector 3 for bending an optical axis and the condensing lens 10 for condensing light may be required. In the photometer 30 of the present embodiment, the first reflector 23 operates for both condensing and reflecting light. Thus, advantageously, the number of the components is reduced, and alignment of an optical axis becomes easy.

Figure 11:
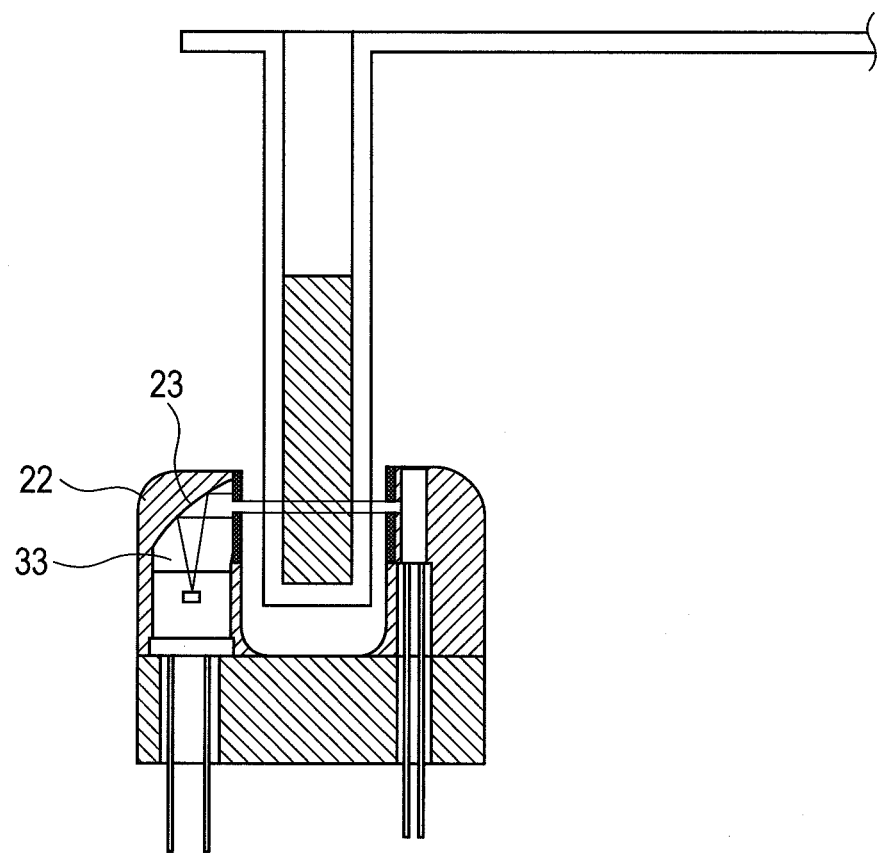
FIG. 11 is a diagram showing a structure of the photometer for the liquid analysis system according to the present invention.

In the example shown in FIG. 10, the first support 22 using a light transmissive member is explained. The first reflector 23 uses its outer surface as a reflection surface. Similarly to Embodiment 1, as shown in FIG. 11, the structure in which an opaque member is used for the first support 22 inside which a space 33 is provided to pass light can be considered. As a result, options for manufacturing the components are increased, and cost reduction is expectable.

Figure 12:
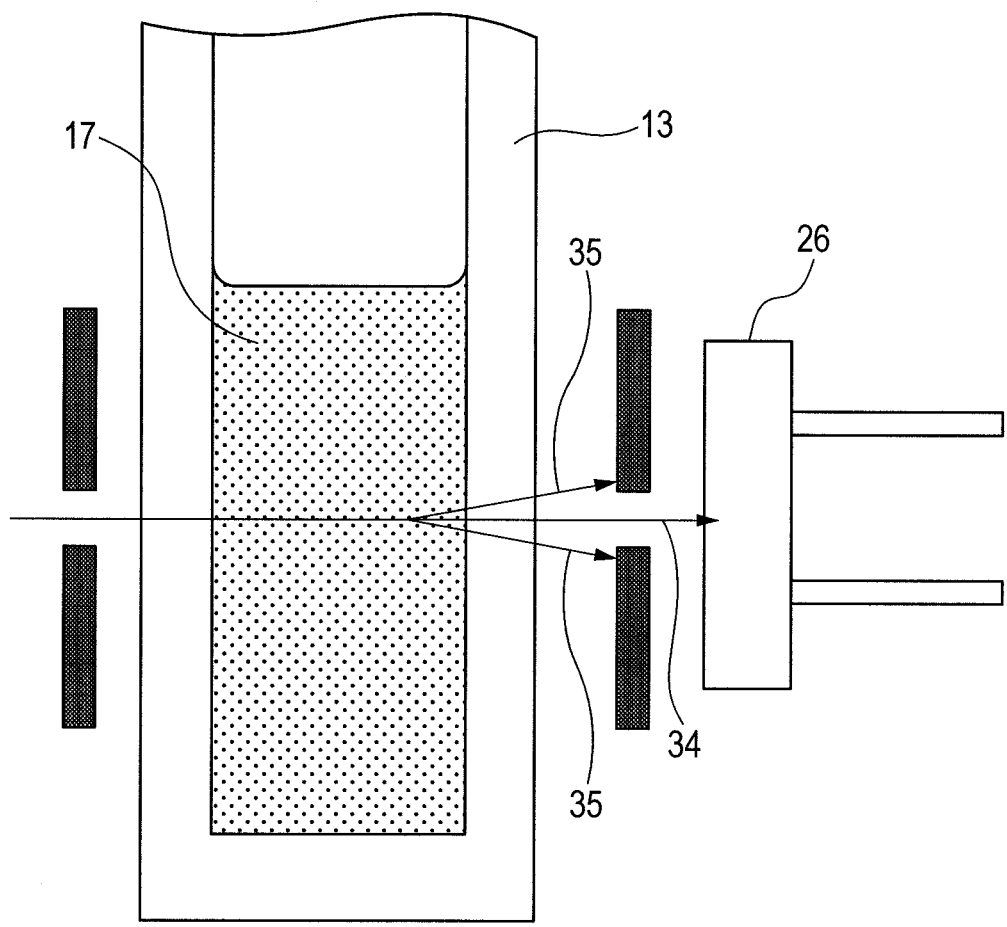
FIG. 12 is a diagram showing a situation in which parallel incident light is scattered.
Figure 13:
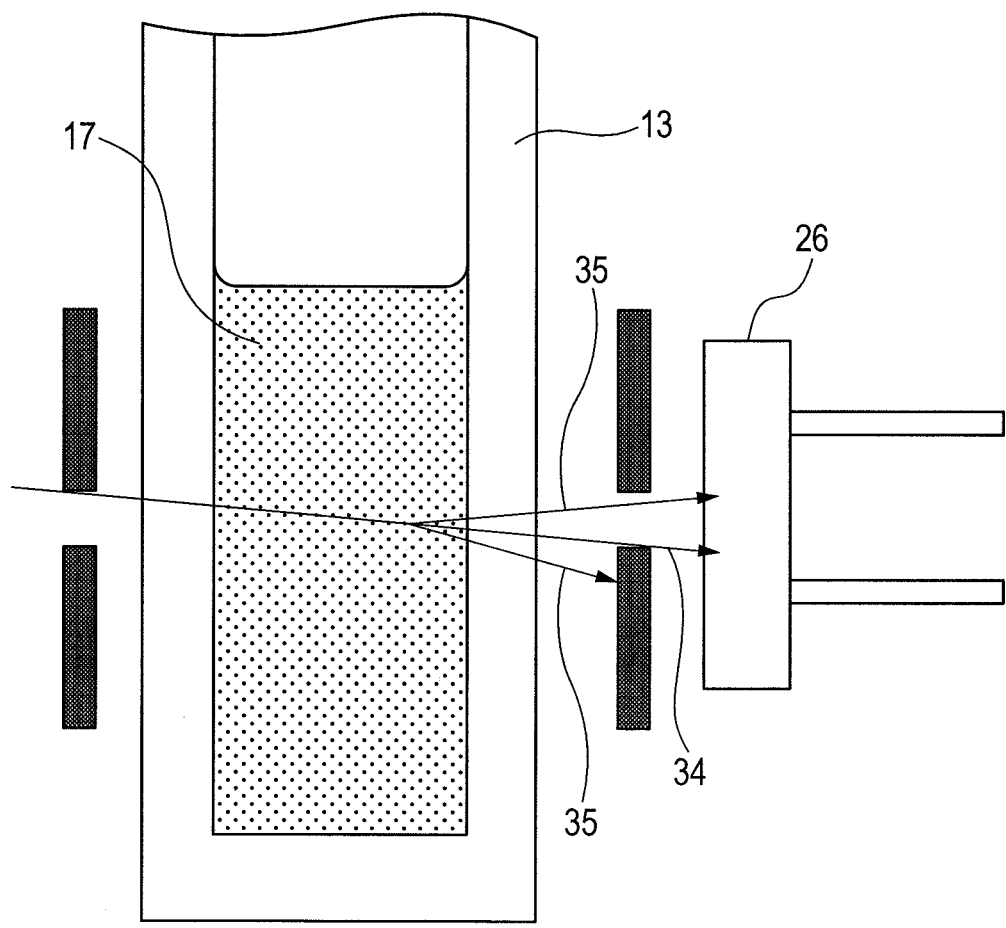
FIG. 13 is a diagram showing a situation in which angular incident light is scattered.

The photometer 30 is advantageous in measurement of scattering light because light that illuminates samples is condensed generally in parallel, as described above. In other words, as shown in FIG. 12, when the measurement sample 17 in the reaction vessel 13 contains an item for measurement using scattered light, a photo detector 26 calculates the amount of scattered light 35 lost from the received transmitted light 34 which has been reduced by dispersion. At this time, it is desirable for the scattered light 35 not to enter the photo detector 26. The scattered light 35 is illumination light emitted by a specific angular distribution. Therefore, when the photometer 11 shown in Embodiment 1 measures scattering light, light may illuminate the measurement sample 17 in the reaction vessel 13 at an angle as shown in FIG. 13. Therefore, the scattered light 35 enters the photo detector 26 easily. As a result, it may be difficult to conduct precise scattering light measurement. In the present photometer 30, light illuminating samples is condensed generally in parallel. It is difficult for the scattering light to enter the photo detector 26. This is advantageous in measurement of scattered light.

Figure 14:
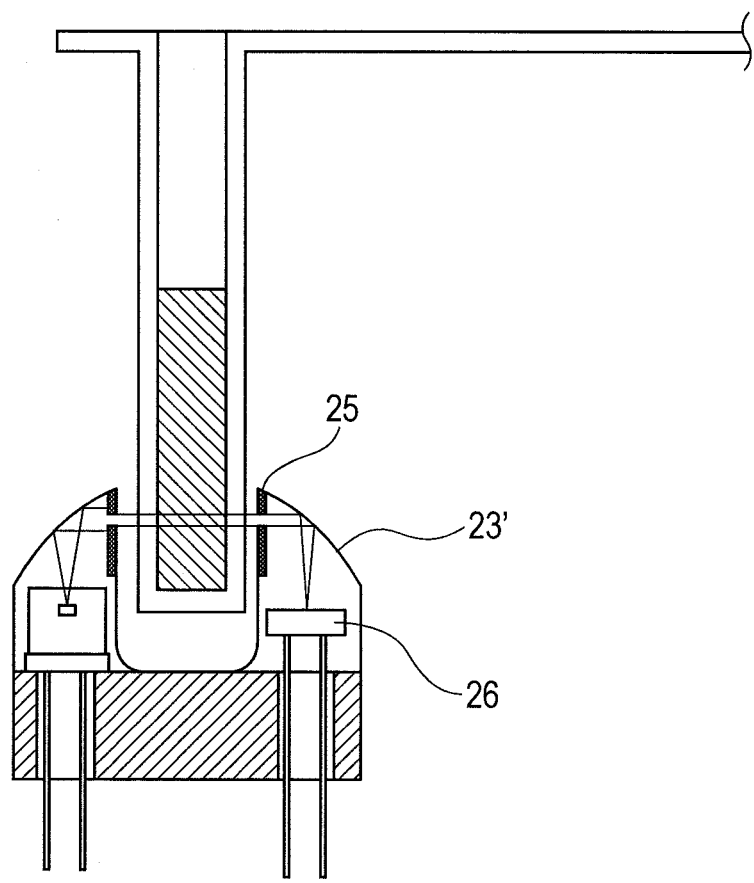
FIG. 14 is a diagram showing a structure of the photometer for the liquid analysis system according to the present invention.
Figure 15:
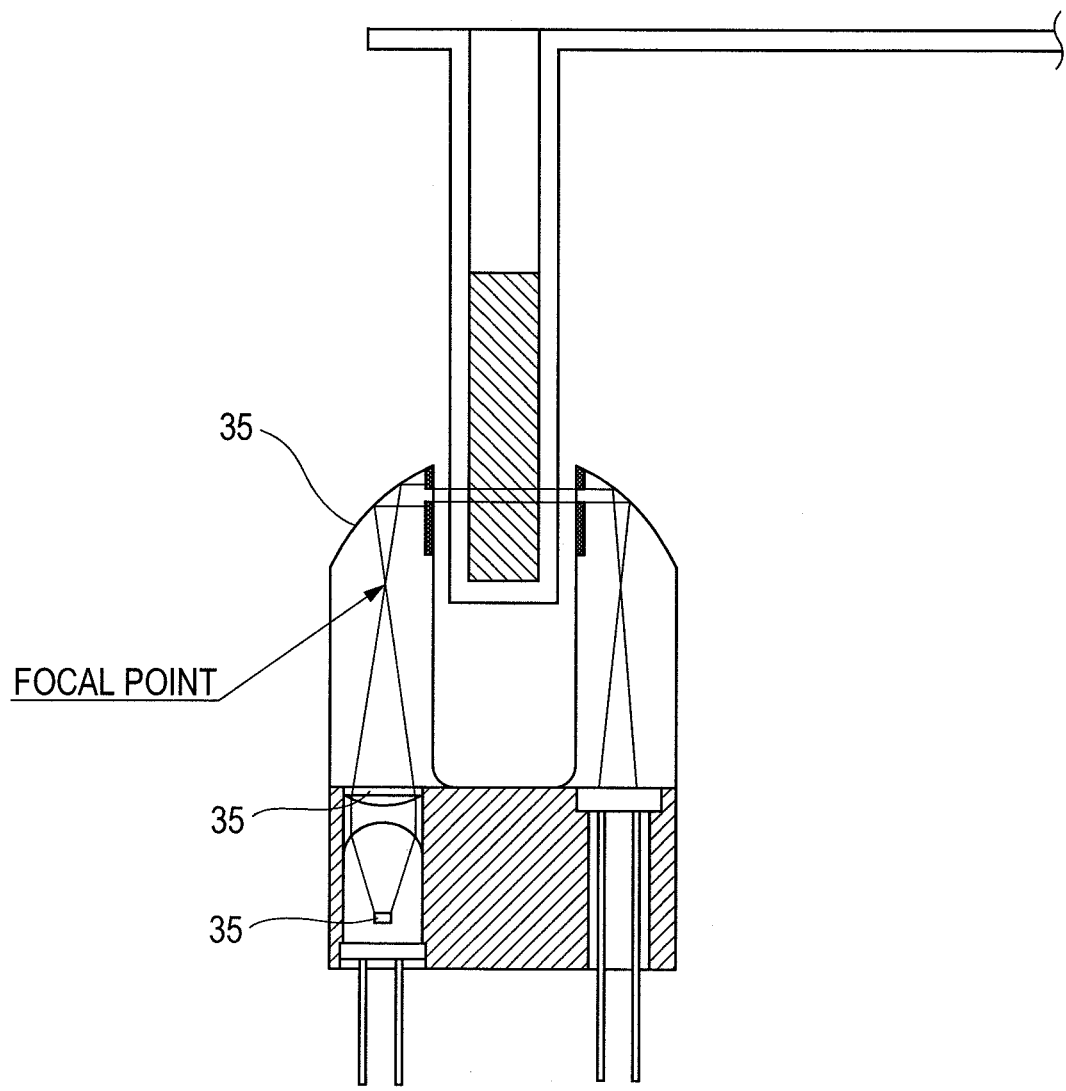
FIG. 15 is a diagram showing a structure of the photometer for the liquid analysis system according to the present invention.

The photo detector 26 is disposed immediately after the second slit 25 in the FIG. 10. Stray light tends to be detected when the second slit 25 and the photo detector 26 are close to one another. As shown in FIG. 14, an optical axis can be bent downward by use of the second reflector 23'. In this case, the second reflector 23' may not be a parabolic mirror. Further, as shown in FIG. 15, an image of light emitted from the LED light source 21 may be formed at a focal point of the parabolic mirror by use of a condensing lens 10'.

(Embodiment 3)

Figure 16:
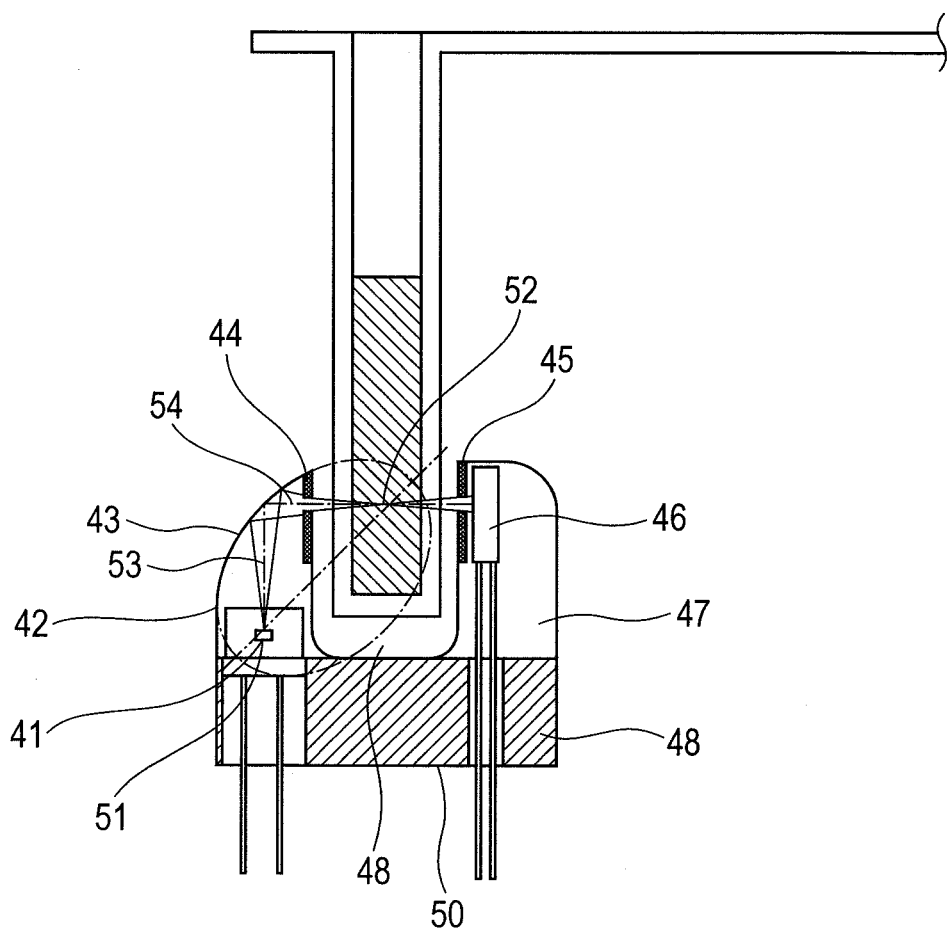
FIG. 16 is a diagram showing a structure of the photometer for the liquid analysis system according to the present invention.

FIG. 16 is a diagram showing a structure of the photometer according to the present invention. The present photometer is a photometer 50 including: an LED source 41; a first support 42 transmitting and passing light emitted from LED source 41 therethrough; a first reflector 43 provided to the first support 42; a first slit 44 provided also to the first support 42; a second support 47 provided with a second slit 45 and a photo detector 46; and a third support 49 connecting the first support 42 and the second support 47 between which a slot 48 is formed. A light emitting diode (LED) is exampled as a light source, but additionally, a semiconductor laser etc. also can be used.

The first reflector 43 is an elliptic mirror defined to be shaped in a partially cut away elliptic mirror and to have a first focal point 51 where the LED source 41 is disposed and a second focal point 52 generally at the center in the longitudinal direction of an optical axis transmitted in the measurement sample 17 in the reaction vessel 13. The optical axis 53 of light emitted from the LED source 41 is set generally vertically, and reflected and bent by the first reflector 43 at a right angle to be a horizontal optical axis 54. To arrange the optical axis 53 of the light emitted from LED source 41 and the horizontal optical axis 54 passing through a sample at a right angle, a long axis of a reference ellipse may be set at 45 degrees relative to the optical axis 53 of emitted light and the horizontal optical axis 54, and a distance between the first focal point 51 and second focal point 52 of the reference ellipse may be the same as a short axis of the reference ellipse. It is important that the optical axis is incident to an optical incidence plane of the reaction vessel 13 at a right angle. It is not necessarily important to reflect and bend the optical axis by use of the first reflector 43 at a right angle. When the optical axis is not bent at a right angle, the optical axis 53 of emitted light is not vertical.

Analysis of measurement samples by the present photometer 50 is conducted by attaching the photometer 50 to the thermostatic bath of the liquid analysis system. The positional relationship between the structure around the portion where the present photometer of the liquid analysis system is attached and the photometer is the same as Embodiment 1 and thus not explained.

Similarly to Embodiment 1, analysis of measurement samples by the present photometer 50 is conducted when the photometer 50 is attached to the thermostatic bath 12, the reaction disk 14 rotates, and the reaction vessel 13 containing the target measurement sample 17 moves to the slot 48 of the photometer 50.

In the analysis, light emitted from the LED source 41 is reflected by the first reflector 43, and illuminates the measurement sample 17 in the reaction vessel 13 with an illumination area controlled to be constant by the first slit 44. The first reflector 43 is an elliptic mirror. Light emitted from the LED source 41 disposed at the first focus 51 of the first reflector 43 is reflected and bent by the first reflector 43 and then condensed to a generally central position in the longitudinal direction of the optical axis transmitted in the measurement sample 17, the generally central position being at the second focal point 52.

Alkali or acid liquid is generally used for constant temperature water 16 to prevent bacterial growth etc. Therefore, the first support 42, the first reflector 43, the first slit 44, the second slit 45, and the third support 49 use glass, metal, and/or resin which are resistant to alkali and acid fluids. The LED source 41, the photo detector 46, etc. are sealed to prevent the intrusion of the constant temperature water 16.

The principle of measurements of samples by the liquid analysis system to which the present photometer is directed is the same as that of Embodiment 1, and thus not explained.

Also in the present photometer 50, radial sizes of the thermostatic bath 12 and reaction vessel disk 14 of the photometer can be reduced relative to the photometer as shown in FIGS. 1 to 4. Similarly to FIG. 7, the multiple reaction vessels 13 arranged on the circumference of the reaction vessel disk 14 can be further arranged in multiple rows concentrically. The processing capability can be improved without changing a size of the system or the system can be improved without changing the processing capability.

In Embodiment 1, the first reflector 3 for bending an optical axis and the condensing lens 10 for condensing light are required. In the photometer 50 of the present embodiment, the first reflector 43 operates for both condensing and reflecting light. The number of the components is reduced to advantageously achieve easy optical axis alignment.

Figure 17:
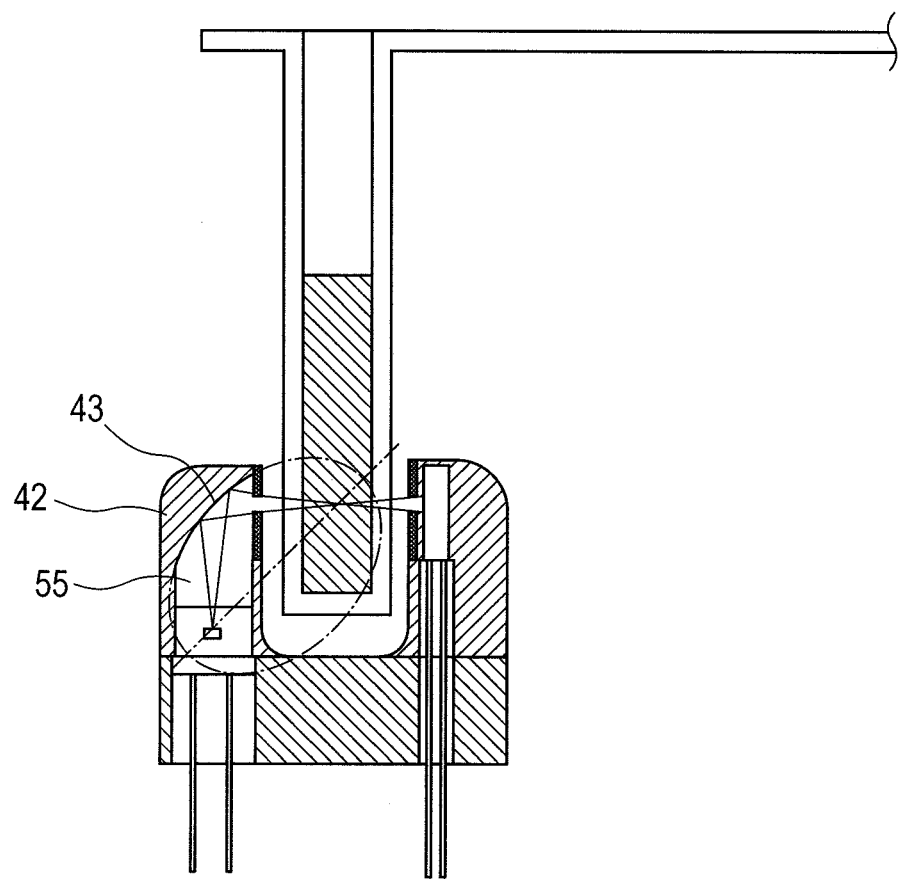
FIG. 17 is a diagram showing a structure of the photometer for the liquid analysis system according to the present invention.

In the example shown in the FIG. 16, the first support 42 is explained by using an optical transmissive member, and the first reflector 43 uses its external surface as a reflection surface. Similarly to Embodiment 1, as shown in FIG. 17, the structure can be also considered in which an opaque member is used for the first support 42 in which a space 55 is provided for passing light therethrough. Accordingly, options of manufacturing components are increased and cost reduction is expectable.

In the photometer 50, as described above, light illuminating a sample is condensed to the generally central position in the longitudinal direction of an optical axis transmitted in the measurement sample 17. Therefore, compared to Embodiments 1 and 2, disadvantage arises in measurement of scattered light, but an amount of received light detected by the photo detector 46 after passing through the first slit 44 and the second slit 45 increases compared to when the light is parallel. This is because, similarly also to Embodiment 1, when light from a light source is made parallel, it is difficult to pass light emitted offset from the light source through both the first slit and the second slit, but when light from the light source is condensed, the light emitted offset from the light source can be condensed easily compared to when the light is parallel.

Figure 18:
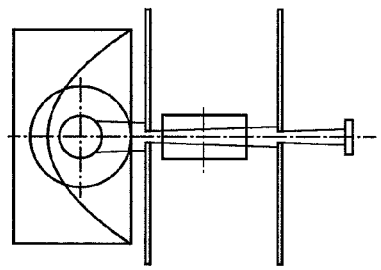
FIG. 18 shows the result of a simulation for the difference in amounts of light by use of a parabolic mirror and an elliptical mirror.
Figure 18:
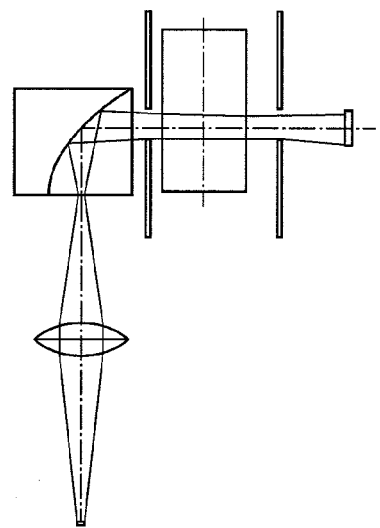
Figure 18:
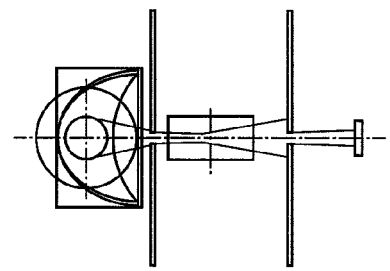
Figure 18:
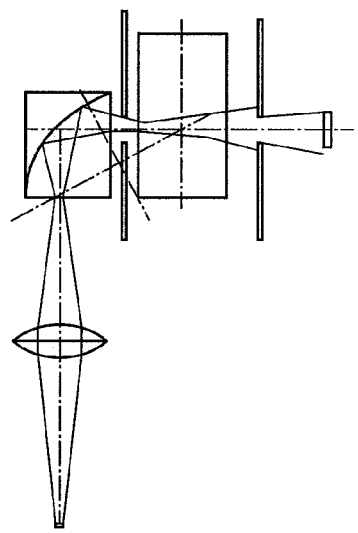

FIG. 18 shown a rate of amounts of received light calculated by comparative simulation when the first reflector is a parabolic mirror and when the first reflector is an elliptic mirror. FIG. 18 (a) shows the case of the parabolic mirror, and FIG. 18 (b) shows the case of the elliptic mirror. As the result of the simulation using an amount and size of emitted light so that both cases are under the generally same condition, when an amount of received light is 1 in the case of the parabolic mirror, an amount of received light is 1.27 in the case of the elliptic mirror. It has been turned out that an amount of light in the case of the elliptic mirror is greater.

Figure 19:
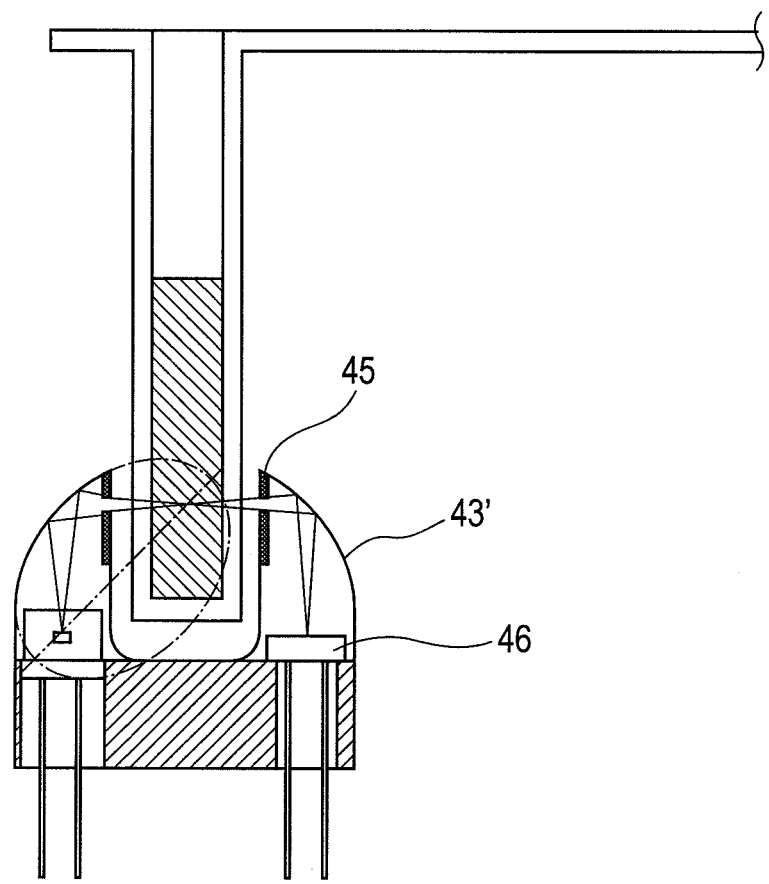
FIG. 19 is a diagram showing a structure of the photometer for the liquid analysis systems according to the present invention.
Figure 20:
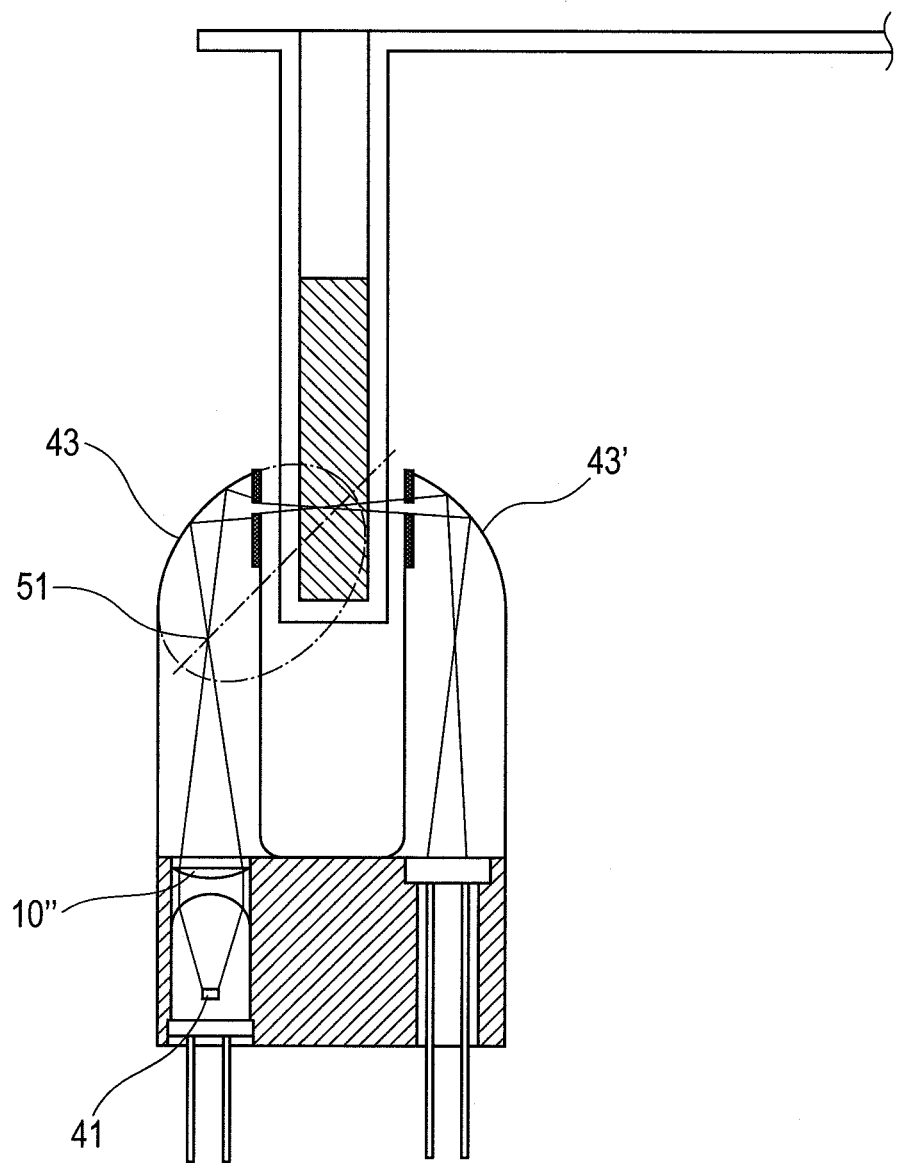
FIG. 20 is a diagram showing a structure of the photometer for the liquid analysis system according to the present invention.
Figure 21:
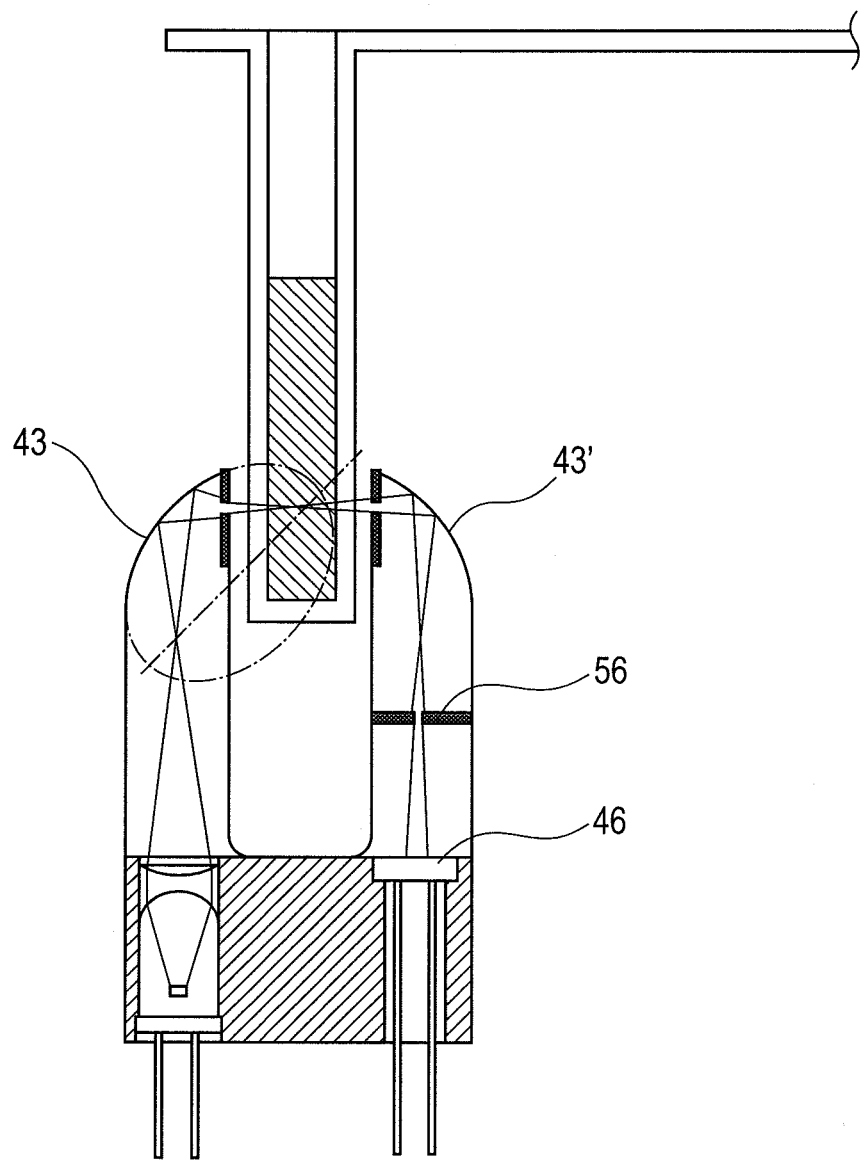
FIG. 21 is a diagram showing a structure of the photometer for the liquid analysis system according to the present invention.

That is, it is suitable to condense light by use of a lens as in Embodiment 1 or by use of, e.g., an elliptic mirror as in Embodiment 3 to conduct a high sensitivity measurement requiring a large amount of light. It is suitable to condense light in parallel as in Embodiment 2 to conduct a measurement using scattered light. The lens and mirrors may be used properly depending on the usage. The photo detector 46 is disposed immediately after the second slit 45 in the FIG. 16. Since stray light is detected easily when the second slit 45 and photo detector 46 are too close to one another, it is also possible to bend an optical axis downward by use of the second reflector 43' as shown in FIG. 19 and FIG. 20. In this case, the second reflector 43' may not be an elliptic mirror. Further, as shown in FIG. 20, an image of light emitted from the LED source 41 is formed at the first focal point 51 of the elliptic mirror by use of a condensing lens 10". To reduce the influence of stray light in scattered light measurement, it is also possible to provide a third slit 56 as shown in FIG. 21.

(Embodiment 4)

Figure 22:
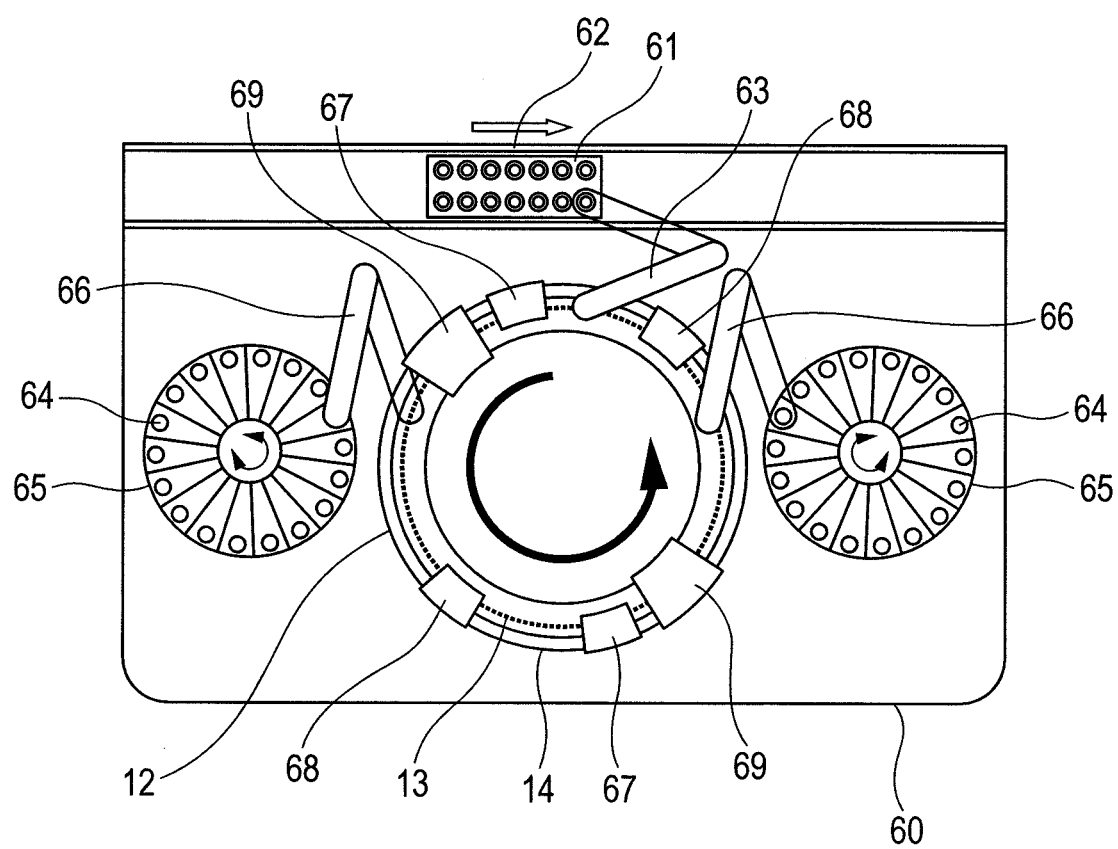
FIG. 22 is a diagram showing a structure of the liquid analysis system according to the present invention.

FIG. 22 is a diagram showing a liquid analysis system 60 of the present embodiment. The liquid analysis system 60 includes: the thermostatic bath 12; a reaction vessel disk 14 having the multiple reaction vessels 13 on the circumference concentric with the thermostatic bath 12; sample containers 61 containing the measurement samples 17; a rack 62 carrying the multiple sample containers 61; a dispenser 63 for sucking the measurement sample 17 by a constant amount and dispensing the sample in the sample container 61 into the reaction vessel disks 13; a reagent disk 65 containing reagent bottles 64 containing multiple reagents selectable depending on analysis items; a reagent dispenser 66 for aspiring a constant amount of a reagent from the reagent bottles 64 and dispensing the reagent to the reaction vessels 13; a stirring section 67 for stirring the measurement samples 17 and reagents dispensed to the reaction vessels 13; a washing section 68 for washing the reaction vessels 13 after analysis; and a measurement section 69 having one or multiple photometers of any one of Embodiments 1, 2, and 3.

In FIG. 22, the reaction vessel disk 14 stops when the measurement samples 17 are dispensed, reagents are dispensed, the measurement sample 17 and reagent dispensed to the reaction vessel 13 are stirred, and the reaction vessels 13 are washed, and rotates and moves to the next reaction vessel 13 for these operations. The rack 62 moves straight to carry the multiple sample containers 61. The reagent disk 65 rotates and moves to a position where the reagent dispenser 66 can aspire the desired reagent bottle 64. Usually, the reaction vessel disk 14 rotates in a certain direction. The measurement sample 17 and the reagent are dispensed. The measurement sample 17 in the reaction vessel 13 is stirred to be measurable and moves to the position of the measurement section 69, and then measured by the desired photometer.

In the liquid analysis system 60, absorption measurements and measurements oriented to scattering characteristics are mixed even in measuring absorptions. In the measurement section 69, multiple photometers 11, multiple photometers 30, and multiple photometers 50 may be mixed and placed depending on purposes. Wavelengths of the multiple photometers may be varied to conduct analyses of multiple items simultaneously.

In this case, arrangement intervals of the arranged photometers are the same as those of the multiple reaction vessels 13 arranged to the reaction vessel disk 14. The multiple measurement samples 17 can be measured by the multiple photometers at the same time. Complicated data processing and device control can be eased and the measurements under the same condition can be conducted.

Reference Signs List
1 . . . LED light source
2 . . . First support
3 . . . First reflector
3' . . . Second reflector
4 . . . First slit
5 . . . Second slit
6 . . . Photo detector
7 . . . Second support
8 . . . Slot
9 . . . Third support
10 . . . Condensing lens
10' . . . Condensing lens
11 . . . Photometer
12 . . . Thermostatic bath
13 . . . Reaction vessel
14 . . . Reaction vessel disk
15 . . . Flow path
16 . . . Constant temperature water
17 . . . Measurement sample
18 . . . Light transmitting space
21 . . . LED light source
22 . . . First support
23 . . . First reflector
23' . . . Second reflector
24 . . . First slit
25 . . . Second slit
26 . . . Photo detector
27 . . . Second support
28 . . . Slot
29 . . . Third support
30 . . . Photometer
31 . . . Horizontal optical axis
32 . . . Optical axis of emitted light
33 . . . Light transmitting space
34 . . . Transmitted light
35 . . . Scattered light
41 . . . LED light source
42 . . . First support
43 . . . First reflector
43' . . . Second reflector
44 . . . First slit
45 . . . Second slit
46 . . . Photo detector
47 . . . Second support
48 . . . Slot
49 . . . Third support
50 . . . Photometer
51 . . . First focal point
52 . . . Second focal point
53 . . . Optical axis of emitted light
54 . . . Optical axis on horizontal portion
55 . . . Light transmitting space
56 . . . Third slit
60 . . . Liquid analysis system
61 . . . Sample container
62 . . . Rack
63 . . . Dispenser
64 . . . Reagent bottle
65 . . . Reagent disk
66 . . . Reagent dispenser
67 . . . Stirring section
68 . . . Washing section
69 . . . Measurement section

The invention claimed is:

1. A photometer comprising:
a light source;
a first support configured to transmit or configured to pass light emitted from the light source therethrough;
a detector configured to detect light passed through a reaction vessel containing a measurement sample;
a second support provided with the detector, the first support and the second support being disposed to enable the reaction vessel containing the measurement sample to be inserted therebetween;
a first reflection section provided to the first support, configured to reflect light emitted from the light source, and configured to pass the light through the reaction vessel, wherein the first reflection part includes a parabolic mirror, and the light source is disposed at a focal point of the parabolic mirror; and
a condensing section configured to condense the light emitted from the light source and configured to pass the light through the reaction vessel.

2. The photometer according to claim 1, wherein the first support includes a first slit configured to pass light reflected by the first reflection section therethrough, and the second support includes a second slit configured to pass light passed through the reaction vessel therethrough.

3. The photometer according to claim 1, wherein the condensing section includes a lens.

4. The photometer according to claim 1, wherein the parabolic mirror functions also as the condensing section.

5. The photometer according to claim 1, wherein the light source includes a semiconductor laser or a light emitting diode.

6. The photometer according to claim 1, wherein the second support transmits or passes light passed through the reaction vessel therethrough, and includes a second reflection section configured to reflect light passed through the reaction vessel into the detector.

7. The photometer according to claim 6, wherein the second support includes a second condensing section configured to condense light passed through the reaction vessel into the detector.

8. The photometer according to claim 7, wherein the second reflection section includes a plane mirror, and the second condensing section includes a lens.

9. The photometer according to claim 6, wherein the second reflection section includes a second parabolic mirror, the second parabolic mirror functions also as the second condensing section, the detector is disposed to a focal point of the second parabolic mirror.

10. The photometer according to claim 6, wherein the second reflection section includes a second elliptic mirror, the second elliptic mirror functions as the second reflection section, and an central position in a longitudinal direction in which the light of the reaction vessel is passed is disposed to a first focal point of the second elliptic mirror, and the detector is disposed at a second focal point of the second elliptic mirror.

11. The photometer according to claim 6, wherein a third slit is provided between the second reflection section and the detector.

12. The photometer according to claim 1, wherein an optical axis of light passed through the reaction vessel is incident vertically onto an optical incident surface of the reaction vessel.

13. The photometer according to claim 1, wherein at least one of the first support and the second support is formed of an optical transmissive member.

14. The photometer according to claim 1, wherein at least one of the first support and the second support is formed of a member having therein a space through which light is passable or a combination of the member and an optical transmissive member.

15. The photometer according to claim 1, wherein the first support and the second support are structured of a material resistant to an acid solution and an alkali solution.

16. An analysis system for an analysis device, the analysis device comprising:
    a reaction vessel configured to contain a measurement sample;
    a thermostatic bath having a constant temperature fluid configured to immerse and hold the reaction vessel; and
    a photometer configured to illuminate the reaction vessel with light, and provided at a bottom portion of the thermostatic bath, the photometer comprising:
    a light source;
    a first support configured to transmit or configured to pass light emitted from the light source therethrough;
    a detector configured to detect light passed through the reaction vessel;
    a second support provided with the detector; and
    a reflection section provided to the first support, configured to reflect light emitted from the light source, and configured to pass the light through the reaction vessel,
    the first support and the second support being disposed to insert the reaction vessel therebetween.

17. The analysis system according to claim 16, further comprising:
    a plurality of photometers arranged at the bottom portion of the thermostatic bath.

18. The analysis system according to claim 17, wherein the plurality of photometers are arranged by combination of a photometer having the reflection section of a plane mirror, a photometer having the reflection section of a parabolic mirror, and a photometer having the reflection section of a elliptic mirror.

19. The analysis system according to claim 17, wherein the thermostatic bath has a ring shape and has a cross section of a U shape, the reaction vessel containing a measurement sample is disposed in a portion of the U shape of the thermostatic bath, the plurality of reaction vessels are arranged on a circumference concentric with the thermostatic bath, and the plurality of photometers are arranged on a circumference concentric with the plurality of reaction vessels.

20. The analysis system according to claim 19, wherein a plurality of combinations of the plurality of reaction vessels arranged on the circumference concentric with the thermostatic bath and the plurality of photometers are arranged on a circumference concentric with the thermostatic bath and having a different diameter from that of the thermostatic bath.

21. The analysis system according to claim 17, wherein the plurality of photometers each have the light source emitting light having a different wavelength.

* * * * *